United States Patent [19]
Schinke et al.

[11] Patent Number: 5,741,976
[45] Date of Patent: Apr. 21, 1998

[54] APPARATUS FOR THE SINGLE-AXIS EXAMINATION OF MICRO-TENSION SAMPLES

[75] Inventors: Bernd Schinke, Bruchsal; Herbert Schneider, Stutensee; Achim Ilzhöfer, Karlsruhe, all of Germany

[73] Assignee: Firschungszeutrwm Karlsruhe GmbH, Karlsruhe, Germany

[21] Appl. No.: 761,773

[22] Filed: Dec. 6, 1996

[51] Int. Cl.$^6$ ..................... G01N 3/08
[52] U.S. Cl. ............... 73/831; 73/826; 73/837
[58] Field of Search ............ 73/826, 831, 832, 73/833, 837, 856, 857, 860

[56] References Cited

U.S. PATENT DOCUMENTS

| | | | |
|---|---|---|---|
| 4,194,402 | 3/1980 | De Nicola | 73/859 |
| 4,686,860 | 8/1987 | Liu | 73/856 |
| 4,730,498 | 3/1988 | Blanch | 73/856 |
| 5,431,060 | 7/1995 | Lauren | 73/856 |

*Primary Examiner*—George M. Dombroske
*Assistant Examiner*—Max H. Noori
*Attorney, Agent, or Firm*—Klaus J. Bach

[57] ABSTRACT

An apparatus for single-axis examinations of micro samples in a tensile testing machine having opposite pull rods between which the apparatus is mounted for the application of tensile forces to a micro-sample includes a load frame for the connection to the pull rods which load frame comprises two parallel spring frame structures in the form of serially arranged cantilever beams defining multiple S structures interconnecting a bottom and a top frame part, sample mounting means mounted on one of the parts, a force measuring element mounted on the other frame part and including hydraulic sample mounting means and flexible means which bend depending on the pulling force applied thereto and which have tension measuring means to measure the bending extent and means for sensing the movement of the second mounting means relative to the one frame part.

1 Claim, 2 Drawing Sheets

APPARATUS FOR THE SINGLE-AXIS EXAMINATION OF MICRO-TENSION SAMPLES

BACKGROUND OF THE INVENTION

The present invention relates to an apparatus for the tensile examination of micro samples in a tensile testing machine.

Material data which are gathered from technological tests with macro samples cannot be transferred directly to conditions as they are present in micro structures. In order to obtain material data and interpretation conditions as they are typical for microstructures, it is necessary to gather the data with correspondingly miniaturized samples.

Accordingly, the present invention is concerned with apparatus for the examination of micro-samples. More specifically the invention is concerned with the single-axis examination of so-called LIGA structures, that is, of microstructures made by a LIGA process and of thin foils by means of a load frame in an appropriate apparatus. It is the object to determine the mechanical tensile properties of structures whose dimensions are in the range of just a few μm. Angle errors or non-axialities of a size which is normal and acceptable for conventional test apparatus render these test apparatus unusable for examination of structures in this size range. However, micro-samples will often be quite stretchable which requires a shape adjustment of the load frame in the main test area. During testing of the samples, it is therefore necessary to insure that the stretch forces are generated solely by the sample and not by the load frame on which the sample is mounted.

It is the object of the present invention to provide a test apparatus which permits a single axis tensile examination of micro-tensile samples.

SUMMARY OF THE INVENTION

An apparatus for single-axis examinations of micro samples in a tensile testing machine having opposite pull rods between which the apparatus is mounted for the application of tensile forces to a micro-sample includes a load frame for the connection to the pull rods, comprising two parallel spring frame structures in the form of serially arranged cantilever beams defining multiple S structures interconnecting a bottom and a top frame part, sample mounting means mounted on one of the parts, a force measuring element mounted on the other frame part and including hydraulic sample mounting means and flexible means which bend depending on the pulling force applied thereto and which have tension measuring means to measure the bending extent and means for sensing the movement of the second mounting means relative to the one frame part.

Additional features of the invention are described below on the basis of the accompanying drawings.

DESCRIPTION OF PREFERRED EMBODIMENTS

Figure 1:
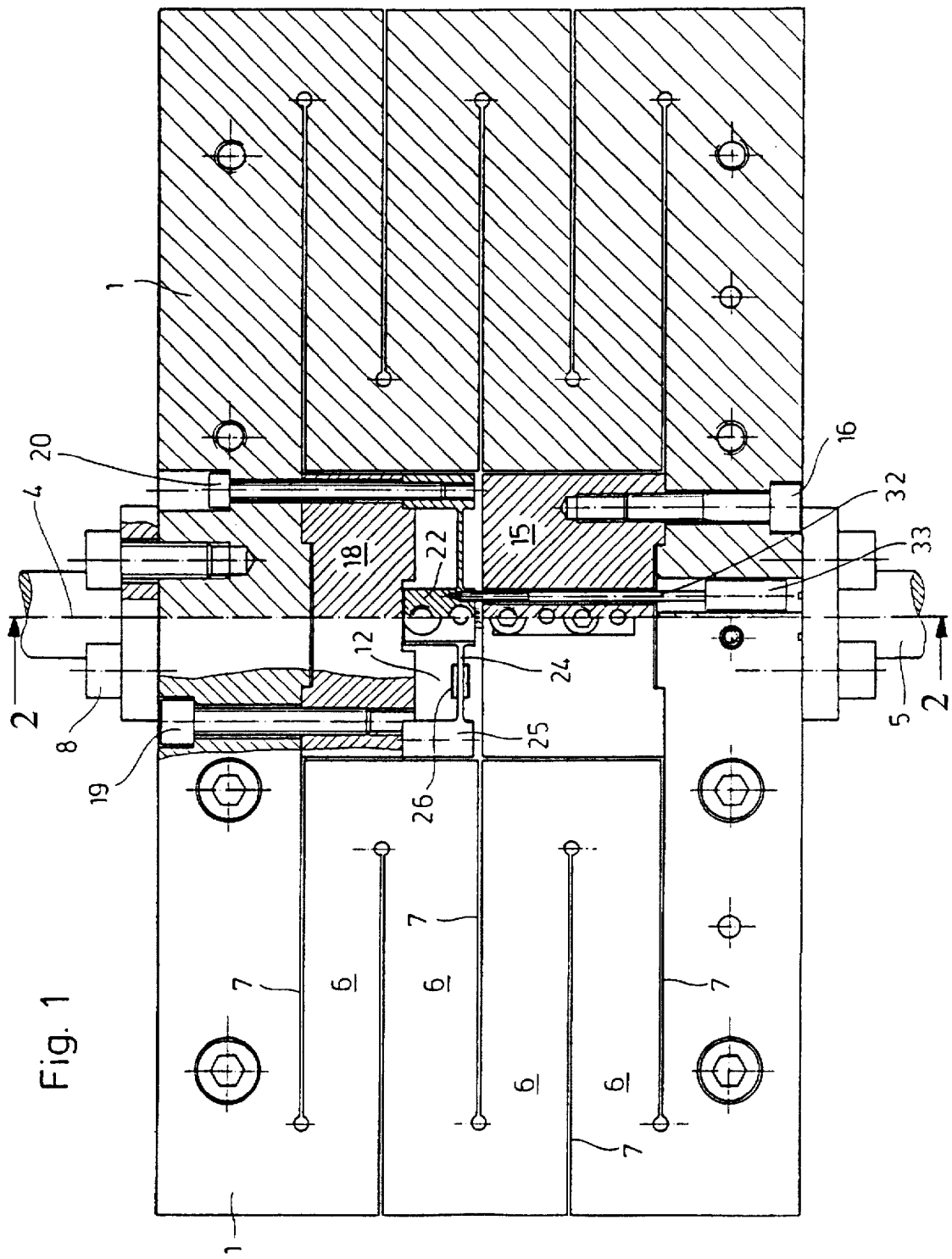
FIG. 1 is a side view showing the apparatus according to the invention partially in cross-section.
Figure 2:
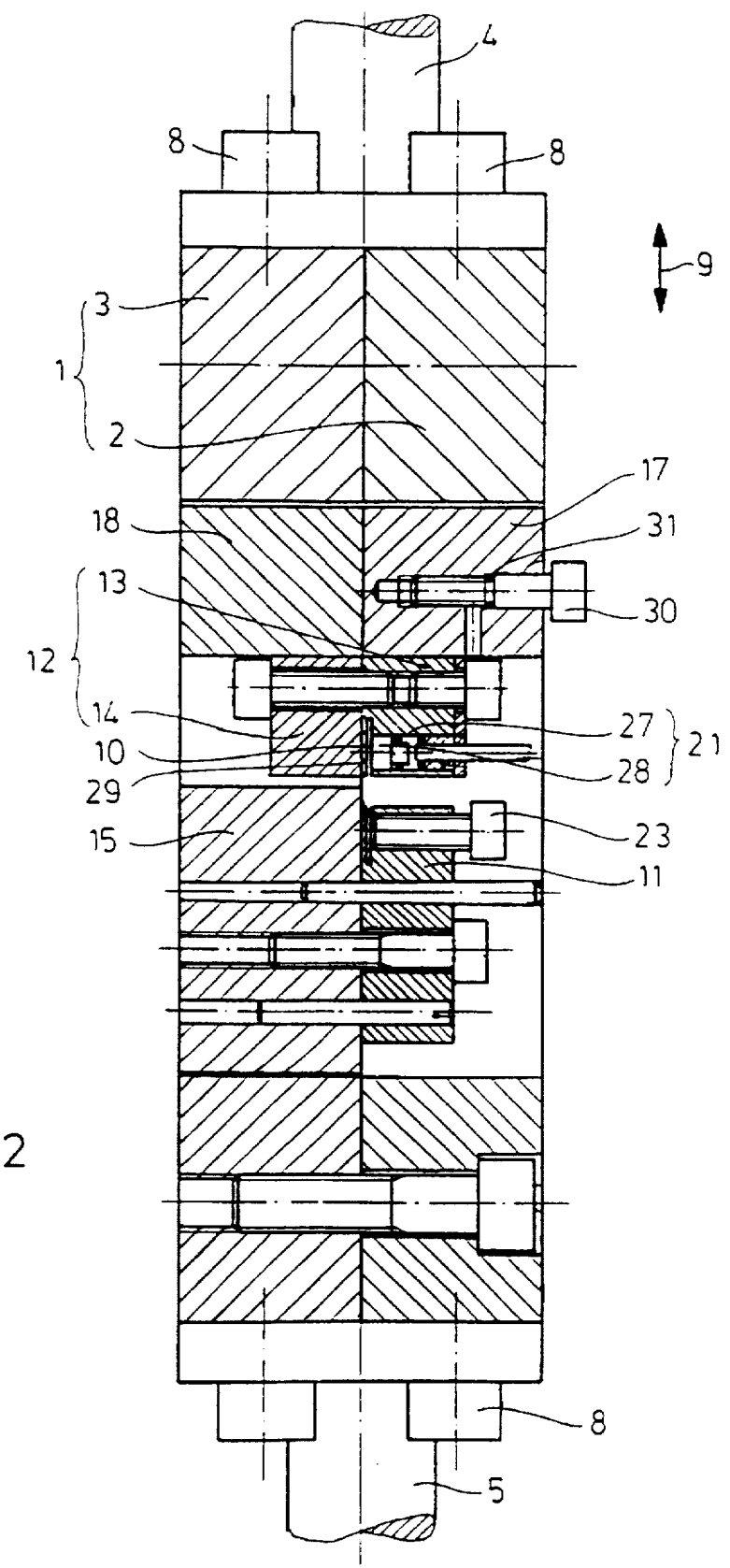
FIG. 2 is a view taken along line 2—2 of FIG. 1.

The most important features of the apparatus according to the invention are the load frame, the force measurement cell and the sample mount. An essential element is the closed load frame 1 which is shown partially in cross-section in FIG. 1 and which comprises a front part 2 (see FIG. 2) and a rear part 3. The load frame 1 is utilized in connection with a tensile testing machine which is not shown in detail as the tensile testing machine with its machine frame is well known and is used only to generate the required tensile testing force. The apparatus according to the invention is connected to the frame of the tensile testing machine by way of an upper pull rod 4 and a lower pull rod 5, the two pull rods 4, 5 being connected to the pull adapters of the tensile testing machine by way of universal joints. The tensile testing machine includes an external force measuring cell which however is not shown as it is part of the well known tensile testing machine. The basic purpose of the load frame 1 is to take up the large forces generated by the tensile testing machine and to provide for a simple easily executable mounting of the sample (in FIG. 2 in the slot 10) of the sample in the load frame. A particular advantage of the load frame 1 is that an eccentric mounting of the sample in the load frame, wherein the sample is loaded in the direction of the arrow 9, has little or no influence on the single directional load force. If the sample would be directly mounted into the frame of the tensile testing machine one would have to make sure that any inclination of the sample is less than 1.7 μm so that the influence of bending forces on the required single direction force application is not excessive.

The front and the rear parts 2 and 3 of the load frame which are bolted together are essentially identical. Both frame parts 2 and 3 have the form of two parallel springs which are generated from a metal plate by wire erosion such that several serially arranged cantilever-like elements 6 with one sided restraints and with intermediate slots 7 are generated in the form of a multiple S. At the top and bottom ends of the load frame 1 bolts 8 are provided for the mounting of the pull rods 4 and 5.

Since the load frame is provided in the form of 2 parallel springs with high spring constants, the sample which is mounted between the two spring structures and which has only a very small spring constant is subjected only to a fraction of the force applied to the load frame. In addition, kinetic energy released upon start-up of the tensile testing machine is taken up by the load frame. In order for the load frame to provide the required expansion with the forces available from the tensile testing machine the rigidity of the frame was reduced by eroding the slots 7 into the frame. Tests have shown that, with a load force on the load frame of 3 kN, the force effective on the sample was about 20N.

The sample which is not shown in the drawings is firmly clamped, with its bottom and top end into the slot 10. The slot 10 is disposed at the interface of the front and the rear parts 2 and 3 of the frame 1. The lower part of the frame 1 includes for that purpose an anvil portion 15 which is supported by means of the bolts 16 and a plate 11 which is bolted onto the anvil portion 15 with a distance corresponding to the width of the slot 10. The gap is accurately provided by the use of gauge strips. The plate 11 includes a clamping bolt 23 by which a sample inserted into the slot 10 can be firmly engaged, via an elastic tongue, between the anvil portion 15 and the plate 11.

The upper part of the load frame 1 includes mounting structures 17 and 18 (front and back) for the two-part force measuring element 12, the mounting structures 17 and 18 being connected to the frame 1 by means of bolts 19. The force measuring element 12 is also supported on the upper part of the frame 1 by bolts 20 (see FIG. 1) and is firmly engaged, at its outer edges, with the mounting structure 18. The force measuring element 12 comprises, in principle, two parts: a front part 13 and a rear part 14. The front part 13 includes a hydraulic mechanism 21 for the upper clamping structure for engaging the upper end of a sample in the slot 10. The clamping structure will be described in greater detail at a later point. The upper part of the slot 10 for engaging the upper end of the sample is disposed between the front part 13 and the rear part 14 of the force measuring element 12. The force measuring element is so shaped that the sample clamping part 22 which is disposed in the middle of the mounting member 25 which is retained by the bolts 20 is slightly movable by bending of the bridge structures 24 extending therebetween. The bridge structures 24 extending between the mounting member 25 and the sample clamping part 22 act like leaf springs. They are provided with tension measuring strips 26 by which the force applied to the sample can be measured by the deformation of the bridge structures 24.

The sample clamping structure integrated on one side into the load frame 1 and on the other side into the force measuring element 12 can be utilized for samples of various thicknesses because of the two part design of the load frame 1 and the force measuring element 12. The sample must not be deformed or bent during clamping; also the clamping structure must not exert any force on the force measuring element. As already mentioned, the upper clamping structure is integrated into the front part 13 of the force measuring element 12. The front part 13 includes a bore 27 in which a sealed piston 28 can be moved by a hydraulic fluid so that the upper end of the sample is firmly engaged in the slot 10 between the clamping tongue 29 and the rear section of the front half of the force measuring element 13. The pressure is generated by turning a bolt 30 into an oil reservoir 31 which is in communication with the bore 27. The upper hydraulic clamping structure prevents that a torque is applied to a sample which is already engaged at the other end thereof so that the sample cannot be bent or pre-tensioned. The two-part frame with a force measuring element which is also divided permits the use of the same load input shaft for any micro-sample by employing gauge strips for width adjustment. If the sample thickness is changed for example by 50 µm a gauge strip of the same thickness is placed into the separation plane between the frame.

Directly coupled with the force measuring element is the travel length measuring system. This system includes an inductive position sensor 33 disposed in the lower part of the load frame. A threaded rod 32 is screwed into the upper resiliently displaceable sample clamping part 22 of the force measuring element 12 and extends downwardly through the anvil portion 15. At its lower end, the threaded rod 32 extends into the position sensor to displace the coil cores of the position sensor which is fixedly attached to the lower part of the load frame 1. In this way, the sample deformation within the load frame is determined by the axial displacement of the coil core. Preferably, two diagonally opposite position sensors 33 are provided in order to compensate for irregularities in the sample plane and in the plane normal thereto.

Basically, the problem with the large force generated by the tensile testing machines in use is solved by installing the load frame in the tensile testing machine. This load frame is sufficiently stiff with regard to the sample but is sufficiently resilient with respect to the tensile testing machine drive. This makes it also possible to accommodate the kinetic energy inherently present in the relatively large tensile testing machine upon operation of the machine, so that the sample is not destroyed thereby.

Basically, the concept of using a load frame involves the use of two spring elements. The separation of the load frame permits the testing of samples of different thicknesses by placing gauge strips of different thickness between the two parts of the load frame. The force measuring system described which is connected to the load frame includes the upper clamping mechanism for the sample and allows for an axial alignment and angular displacement which could not be achieved otherwise. The load frame can easily be installed into conventional material testing machines.

What is claimed is:

1. An apparatus for single-axis examination of micro-tension samples in a tensile testing machine having opposite pull rods between which said apparatus is mounted for the application of tensile forces to said micro-tension samples; said apparatus comprising:

a load frame for connection to said opposite pull rods, said load frame having a front and a rear frame part and comprising two parallel spring structures in the form of serially arranged cantilevered beams defining multiple S structures with slots formed between adjacent beams, said spring structures interconnecting a bottom and a top frame part with some resiliency, mechanical first mounting means for engaging and firmly holding one end of a micro-tension sample mounted on one of said frame parts, a force measuring dement mounted on the other of said frame parts and including hydraulic second mounting means for engaging and holding the other end of said micro-tension sample, said force measuring element including flexible means which bend depending on a pulling force applied thereto, tension measuring means on said force measuring element for sensing the pulling force applied to said micro-tension sample by said second mounting means, and means for sensing any movement of said second mounting means relative to said one frame part.

* * * * *